United States Patent
Yan et al.

(10) Patent No.: US 9,546,189 B2
(45) Date of Patent: Jan. 17, 2017

(54) SURFACE MODIFIED LITHIUM TITANATE AND PREPARATION METHOD THEREOF

(71) Applicant: Ningde Amperex Technology Ltd., Ningde, Fujian Province (CN)

(72) Inventors: Chuanmiao Yan, Ningde (CN); Kaifu Zhong, Ningde (CN)

(73) Assignee: NINGDE AMPEREX TECHNOLOGY LTD., Ningde (CN)

( * ) Notice: Subject to any disclaimer, the term of this patent is extended or adjusted under 35 U.S.C. 154(b) by 437 days.

(21) Appl. No.: 14/072,445

(22) Filed: Nov. 5, 2013

(65) Prior Publication Data

US 2014/0252267 A1 Sep. 11, 2014

(30) Foreign Application Priority Data

Mar. 6, 2013 (CN) .......................... 2013 1 0071128

(51) Int. Cl.

| | |
|---|---|
| *C07F 9/09* | (2006.01) |
| *C07F 9/28* | (2006.01) |
| *H01M 4/60* | (2006.01) |
| *C07F 9/53* | (2006.01) |
| *C07F 9/32* | (2006.01) |
| *C07F 9/40* | (2006.01) |
| *H01M 4/36* | (2006.01) |
| *H01M 4/485* | (2010.01) |
| *H01M 4/62* | (2006.01) |
| *H01M 4/131* | (2010.01) |
| *H01M 10/42* | (2006.01) |

(52) U.S. Cl.
CPC ............... *C07F 9/091* (2013.01); *C07F 9/327* (2013.01); *C07F 9/3211* (2013.01); *C07F 9/4006* (2013.01); *C07F 9/4015* (2013.01); *C07F 9/5304* (2013.01); *H01M 4/366* (2013.01); *H01M 4/485* (2013.01); *H01M 4/62* (2013.01); *H01M 4/131* (2013.01); *H01M 10/4235* (2013.01); *Y02E 60/122* (2013.01)

(58) Field of Classification Search
CPC .................................................... H01M 4/382
See application file for complete search history.

(56) References Cited

U.S. PATENT DOCUMENTS 3,965,071 A * 6/1976 McClelland ........... C08G 63/85 528/279
5,656,716 A * 8/1997 Schmidt ................. C08G 63/85 502/150

* cited by examiner

*Primary Examiner* — Peter F Godenschwager
(74) *Attorney, Agent, or Firm* — Arent Fox LLP

(57) ABSTRACT

A surface modified lithium titanate and preparation method thereof is provided. In the surface modified lithium titanate, the deactivating groups distributed on the surface of the lithium titanate are —O—P—RR'R", —O—P—(OR)R'R", —O—P—(OR)(OR')R", and —O—P—(OR)(OR')(OR"), where R, R' and R" are identical or different C1~C8 alkyl or alkenyl groups. The deactivating groups are bonded to the lithium titanate via a bond or a bridge. The exemplary surface modified lithium titanate can effectively lower its catalytic activity, reduce the gassing of lithium ion batteries, and therefore improve the high temperature storage and high temperature cycle performance of lithium titanate batteries. The exemplary preparation method is simple, has great repeatability, a low cost, low pollution to the environment, and is suitable for industrial production.

6 Claims, 1 Drawing Sheet

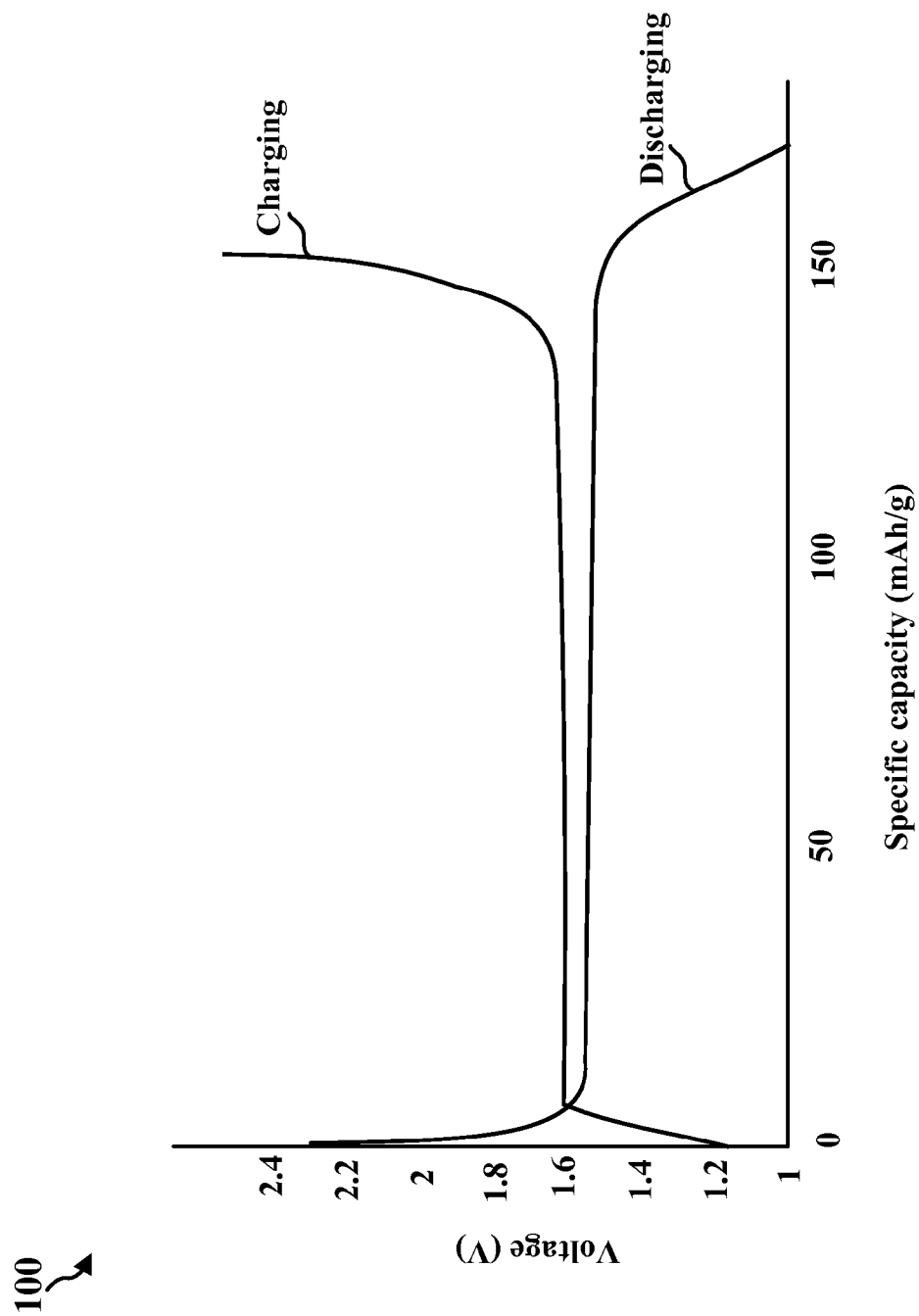

SURFACE MODIFIED LITHIUM TITANATE AND PREPARATION METHOD THEREOF

CROSS-REFERENCE TO RELATED APPLICATION(S)

This application claims the benefit of Chinese Patent Application No. CN201310071128, entitled "Surface Modified Lithium Titanate and Preparation Method Thereof" and filed on Mar. 6, 2013 in the State Intellectual Property Office of the People's Republic of China (PRC) (SIPO), the disclosure of which is expressly incorporated by reference herein in its entirety.

BACKGROUND

Field

The present disclosure relates generally to lithium titanate, and more particularly, to a surface modified lithium titanate and preparation method thereof.

Background

When lithium titanate, as a zero strain material, is used as a cathodic material for a lithium ion battery, the lithium ion battery has excellent cycle performance and relatively long service life. Studies have found that when lithium titanate is used as the cathodic material, the cycle life of the lithium ion battery at normal temperature may reach more than 20,000 times, which results in an excellent prospect for the application of lithium titanate in a lithium ion battery. In addition, lithium ion batteries that use lithium titanate as the cathodic material (hereinafter the "lithium titanate battery") have features of a stable discharge voltage and a high voltage plateau, and do not cause lithium precipitation. Accordingly, lithium titanate batteries are very safe, and therefore offer great advantages for applications in electric automobiles. However, lithium titanate batteries have poor cycle performance at high temperatures, and could produce a relatively large amount of gas, leading to a greatly shortened service life.

Therefore, there is a need for a surface modified lithium titanate for reducing the catalytic activity of lithium titanate, thereby significantly improving the gassing issue in lithium titanate batteries and improving the high temperature performance of lithium titanate batteries.

SUMMARY

A surface modified lithium titanate and preparation method thereof is provided that can reduce the catalytic activity of lithium titanate particles, thereby reducing the gassing of lithium ion batteries and further improving the high temperature storage and cycle performance of lithium ion batteries.

According to a first aspect, a surface modified lithium titanate is provided in which the deactivating groups that are distributed on the surface of the lithium titanate are —O—P—RR'R", —O—P—(OR)R'R", —O—P—(OR)(OR')R", and —O—P—(OR)(OR')(OR"), where R, R' and R" are identical or different C1~C8 alkyl or alkenyl groups, and the deactivating groups are bonded to lithium titanate via a bond or a bridge.

According to the second aspect, a method for preparing surface modified lithium titanate is provided for preparing the surface modified lithium titanate. The method includes the steps of dissolving lithium titanate particles in a first anhydrous organic solvent to obtain a suspension; adding an organic phosphorus compound into the suspension; when the reaction is completed, filtering the suspension through suction; washing the solid obtained from the suction filtration with a second anhydrous organic solvent; and obtaining the surface modified lithium titanate after drying in an oven. The organic phosphorus compound is a phosphine oxide compound represented by the general formula (1) of O=P—RR'R", a phosphinate ester compound represented by the general formula (2) of O=P—(OR)R'R", a phosphonate ester compound represented by the general formula (3) of O=P—(OR)(OR')R", or a phosphate ester compound represented by the general formula (4) of O=P—(OR)(OR')(OR"), where R, R' and R" are identical or different C1~C8 alkyl or alkenyl groups, respectively.

The exemplary surface modified lithium titanate and preparation method thereof has the following advantageous effects: The exemplary surface modification of lithium titanate can keep lithium titanate away from contacting other molecules, effectively lowering its catalytic activity, reducing the gassing of lithium ion batteries, and therefore improving the high temperature storage and high temperature cycle performance of lithium titanate batteries. Further, the exemplary preparation method is simple, has great repeatability, a low cost, low pollution to the environment, and is suitable for industrial production.

BRIEF DESCRIPTION OF THE DRAWINGS

FIG. 1 illustrates charging and discharging cycle curves of a button battery assembled with the exemplary surface modified lithium titanate in Example 1.

DETAILED DESCRIPTION

As discussed supra, lithium titanate batteries have poor cycle performance at high temperatures, and could produce a relatively large amount of gas, leading to a greatly shortened service life.

Currently, the gas production is inhibited mostly with coating methods. CN102376947A provides a method for coating nano-lithium titanate composite material with aluminum oxide, which inhibits the gassing of lithium titanate battery during storage and cycle by coating a uniform aluminum oxide layer. CN101764209A provides a lithium titanate composite electrode material having a surface coating, which coats lithium titanate with oxides, phosphates, and $LiMPO_4$ (where M is magnesium, iron, cobalt, nickel, chromium, titanium, or vanadium) so as to form a protective film on the surface, thereby changing the surface physical properties and chemical properties of the lithium titanate active material, reducing the reaction with electrolyte solution and then reducing gassing. The coating of lithium titanate can inhibit the gas production to a certain degree. Due to the presence of some uncoated reaction active sites as a result of an incomplete coating, however, these active sites can still contact and react with the electrolyte solution. Therefore, the surface coating is unable to fundamentally solve this problem.

Lithium titanate has a valence state of +4 when not charged and the valence state of part of the lithium titanate changes from +4 to +3 during the charging process. Such a mutual conversion of valence states leads to a relatively strong catalytic activity and results in gas production in lithium ion batteries. As a result, reducing the catalytic activity of titanium plays a critical role in gas production, high temperature storage, and high temperature cycle performance of lithium titanate batteries. If the catalytic activity of lithium titanate particles can be reduced through surface modification of lithium titanate particles, the gas production of lithium ion batteries will be effectively controlled, and the high temperature performance of lithium ion batteries will then be improved. The exemplary surface modified lithium titanate and preparation method thereof, as well as examples thereof, are described infra in detail.

A surface modified lithium titanate according to a first aspect will be described. The surface modified lithium titanate according to the first aspect includes deactivating groups distributed on the surface of the lithium titanate. The deactivating groups distributed on the surface of the lithium titanate are —O—P—RR'R", —O—P—(OR)R'R", —O—P—(OR)(OR')R", and —O—P—(OR)(OR')(OR"), where R, R' and R" are identical or different C1~C8 alkyl or alkenyl groups. The deactivating groups are bonded to lithium titanate via a bond or a bridge. Coordination bonds are formed in the form of shared electron pairs between the deactivating groups and lithium titanate particles. The presence of the coordinate bonds stabilizes titanium, weakens the contact of lithium titanate with other molecules, and greatly reduces the catalytic activity of lithium titanate, thereby reducing the gas production thereof, reducing the thickness of expansion of the core during high temperature storage and high temperature cycle, and consequently improving the high temperature storage and high temperature cycle performance of lithium titanate batteries.

In the surface modified lithium titanate according to the first aspect, the lithium titanate may be one or more of pure lithium titanate, lithium titanate having a surface coating, and/or doped lithium titanate. In the surface modified lithium titanate according to the first aspect, the surface coating may be a metal oxide or composite oxide thereof; one or more of aluminum phosphate, magnesium phosphate, lithium fluoride, or lithium phosphate; or $LiMPO_4$. The metal in the metal oxide or composite oxide may be magnesium (Mg), aluminum (Al), silicon (Si), titanium (Ti), vanadium (V), zirconium (Zr), scandium (Sc), manganese (Mn), chromium (Cr), cobalt (Co), nickel (Ni), zinc (Zn), or cerium (Ce). The M in $LiMPO_4$ may be Mg, iron (Fe), Co, Ni, Cr, Ti, or V. In the surface modified lithium titanate according to the first aspect, the doped lithium titanate may be lithium titanate doped with one or more of niobium (Nb), Mg, Zn, lanthanum (La), Zr, nitrogen (N), Al, or yttrium (Y) ions.

In the surface modified lithium titanate according to the first aspect, a particle size of the lithium titanate with a surface coating may be greater than or equal to 10 nm and less than or equal to 100 μm. In one configuration, the particle size of the lithium titanate with the surface coating is greater than or equal to 50 nm and less than or equal to 1000 nm (1 μm). In the surface modified lithium titanate according to the first aspect, the alkyl group may be at least one of methyl, ethyl, n-propyl, isopropyl, or n-octyl groups. The alkenyl group may be the ethylene group.

The method for preparing the surface modified lithium titanate according to a second aspect will be described. The method for preparing the surface modified lithium titanate according to the second aspect is used to prepare the surface modified lithium titanate according to the first aspect. The method includes dissolving lithium titanate particles in a first anhydrous organic solvent to obtain a suspension; adding an organic phosphorus compound into the suspension; filtering the suspension through suction when the reaction is completed; washing the solid obtained from the suction filtration with a second anhydrous organic solvent; and obtaining the surface modified lithium titanate after drying in an oven. The organic phosphorus compound may be a phosphine oxide compound represented by the general formula (1) of O=P—RR'R", a phosphinate ester compound represented by the general formula (2) of O=P—(OR)R'R", a phosphonate ester compound represented by the general formula (3) of O=P—(OR)(OR')R", or a phosphate ester compound represented by the general formula (4) of O=P—(OR)(OR')(OR"), where R, R', and R" are identical or different C1~C8 alkyl or alkenyl groups, respectively.

In the method for preparing the surface modified lithium titanate according to the second aspect, the steps of filtering the suspension through suction and washing the solid obtained from the suction filtration with a second anhydrous organic solvent suspension may be repeated 2-3 times before drying in an oven to obtain the surface modified lithium titanate.

In the method for preparing the surface modified lithium titanate according to the second aspect, the amount of organic phosphorous compound added to the suspension should not be too low, otherwise it may be impossible to form very good deactivating groups on the surface of lithium titanate particles. The amount of organic phosphorous compound added to the suspension should not be too high, either, otherwise it may cause unnecessary waste of the organic phosphorous compound. In one configuration, the mass ratio of the organic phosphorous compound to the lithium titanate particles is (0.01-10):100.

In the method for preparing the surface modified lithium titanate according to the second aspect, the first anhydrous organic solvent and the second anhydrous organic solvent may be at least one of anhydrous ethanol, anhydrous methanol, anhydrous isopropanol, or anhydrous N-methylpyrrolidone. The first anhydrous organic solvent and the second anhydrous organic solvent may be identical or different. These solvents may reduce water present in the reaction system, thereby reducing water entering the lithium titanate particles.

In the method for preparing the surface modified lithium titanate according to the second aspect, the organic phosphorus compound represented by the general formula (1) may comprise trimethylphosphine oxide and methyl ethyl n-propylphosphine oxide; the organic phosphorus compound represented by the general formula (2) may comprise diethyl methylphosphinate, diisopropyl ethylphosphinate, and diethenyl n-propylphosphinate; the organic phosphorus compound represented by the general formula (3) may comprise n-octyl methyl ethylphosphonate, and ethenyl dimethylphosphonate; and the organic phosphorus compound represented by the general formula (4) may comprise trimethyl phosphate, methyl ethyl n-propyl phosphate, and dimethyl ethyl phosphate.

In the method for preparing the surface modified lithium titanate according to the second aspect, the step of adding the organic phosphate into the suspension may be added with stirring, and the stirring time after the addition may be 10 min-3 h.

Examples, comparison examples, and testing results of the surface modified lithium titanate and preparation method thereof will be described.

Example 1

In a dry atmosphere, add 50 g of lithium titanate particles with a particle size of 10 nm into 250 mL of anhydrous ethanol, and then stir at a rotation speed of 500 rpm for 30 min to obtain a homogeneously dispersed suspension. While stirring, add trimethyl phosphate (where the mass ratio of trimethyl phosphate to lithium titanate is 0.01:100), and when the addition is completed, keep the rotation speed constant to continue stirring for 3 h. When the reaction is completed, filter the reacted suspension through suction, place the solid obtained from the suction filtration into a beaker, add 100 mL of anhydrous ethanol to wash, stir to disperse the solid, and then filter through suction. Repeat the filtering steps three times. Subsequently, dry in an oven to obtain the surface deactivated lithium titanate.

The deactivating groups with the structural formula of —O—P—$(OCH_3)_3$ are distributed on the surface of lithium titanate, and the deactivating groups are bonded with lithium titanate particles through the bond of Ti—O—P—$(OCH_3)_3$ and the bridge of $(Ti—O)_2P$—$(OCH_3)_3$.

Example 2

In a dry atmosphere, add 50 g of lithium titanate particles with a particle size of 50 nm into 250 mL of anhydrous methanol, and then stir at a rotation speed of 500 rpm for 30 min to obtain a homogeneously dispersed suspension. While stirring, add n-octyl methyl ethylphosphonate (where the mass ratio of n-octyl methyl ethylphosphonate to lithium titanate is 0.1:100), and when the addition is completed, keep the rotation speed constant to continue stirring for 1 h. When the reaction is completed, filter the reacted suspension through suction, place the solid obtained from the suction filtration into a beaker, add 100 mL of anhydrous isopropanol to wash, stir to disperse the solid, and then filter through suction. Repeat the filtering steps three times. Subsequently, dry in an oven to obtain the surface deactivated lithium titanate.

The deactivating groups with the structural formula of —O—P—$(C_7H_{14}CH_3)(OCH_2CH_3)(OCH_3)$ are distributed on the surface of lithium titanate, and the deactivating groups are bonded with lithium titanate particles through the bond of Ti—O—P—$(C_7H_{14}CH_3)(OCH_2CH_3)(OCH_3)$ and the bridge of $(Ti—O)_2P$—$(C_7H_{14}CH_3)(OCH_2CH_3)(OCH_3)$.

Example 3

In a dry atmosphere, add 50 g of lithium titanate particles with a particle size of 100 nm into 250 mL of anhydrous N-methylpyrrolidone, and then stir at a rotation speed of 500 rpm for 30 min to obtain a homogeneously dispersed suspension. While stirring, add diethyl methylphosphinate (where the mass ratio of diethyl methylphosphinate to lithium titanate is 1:100), and when the addition is completed, keep the rotation speed constant to continue stirring for 0.5 h. When the reaction is completed, filter the reacted suspension through suction, place the solid obtained from the suction filtration into a beaker, add 100 mL of anhydrous isopropanol to wash, stir to disperse the solid, and then filter through suction. Repeat the filtering steps three times. Subsequently, dry in an oven to obtain the surface deactivated lithium titanate.

The deactivating groups with the structural formula of —O—P—$(CH_2CH_3)_2(OCH_3)$ are distributed on the surface of lithium titanate, and the deactivating groups are bonded with lithium titanate particles through the bond of Ti—O—P—$(CH_2CH_3)_2(OCH_3)$ and the bridge of $(Ti—O)_2P$—$(CH_2CH_3)_2(OCH_3)$.

Example 4

In a dry atmosphere, add 50 g of lithium titanate particles with a particle size of 100 nm into 250 mL of anhydrous methanol, and then stir at a rotation speed of 500 rpm for 30 min to obtain a homogeneously dispersed suspension. While stirring, add trimethylphosphine oxide (where the mass ratio of trimethylphosphine oxide to lithium titanate is 2:100), and when the addition is completed, keep the rotation speed constant to continue stirring for 10 min. When the reaction is completed, filter the reacted suspension through suction, place the solid obtained from the suction filtration into a beaker, add 100 mL of anhydrous methanol to wash, stir to disperse the solid, and then filter through suction. Repeat the filtering steps three times. Subsequently, dry in an oven to obtain the surface deactivated lithium titanate.

The deactivating groups with the structural formula of —O—P—$(CH_3)_3$ are on the modified surface of lithium titanate, and the deactivating groups are bonded with lithium titanate particles through the bond of Ti—O—P—$(CH_3)_3$ and the bridge of $(Ti—O)_2P$—$(CH_3)_3$.

Example 5

In a dry atmosphere, add 50 g of lithium titanate particles with a particle size of 1000 nm into 250 mL of anhydrous isopropanol, and then stir at a rotation speed of 500 rpm for 30 min to obtain a homogeneously dispersed suspension. While stirring, add methyl ethyl n-propylphosphine oxide (where the mass ratio of methyl ethyl n-propylphosphine oxide to lithium titanate is 3:100), and when the addition is completed, keep the rotation speed constant to continue stirring for 3 h. When the reaction is completed, filter the reacted suspension through suction, place the solid obtained from the suction filtration into a beaker, add 100 mL of anhydrous isopropanol to wash, stir to disperse the solid, and then filter through suction. Repeat the filtering steps three times. Subsequently, dry in an oven to obtain the surface deactivated lithium titanate.

The deactivating groups with the structural formula of —O—P—$(CH_3)(CH_2CH_3)(CH_2CH_2CH_3)$ are distributed on the surface of lithium titanate, and the deactivating groups are bonded with lithium titanate particles through the bond of Ti—O—P—$(CH_3)(CH_2CH_3)(CH_2CH_2CH_3)$ and the bridge of $(Ti—O)_2P$—$(CH_3)(CH_2CH_3)(CH_2CH_2CH_3)$.

Example 6

In a dry atmosphere, add 50 g of lithium titanate particles with a particle size of 100 μm into 250 mL of anhydrous N-methylpyrrolidone, and then stir at a rotation speed of 500 rpm for 30 min to obtain a homogeneously dispersed suspension. While stirring, add diisopropyl ethylphosphinate (where the mass ratio of diisopropyl ethylphosphinate to lithium titanate is 5:100), and when the addition is completed, keep the rotation speed constant to continue stirring for 1 h. When the reaction is completed, filter the reacted suspension through suction, place the solid obtained from the suction filtration into a beaker, add 100 mL of anhydrous N-methylpyrrolidone to wash, stir to disperse the solid, and then filter through suction. Repeat the filtering steps three times. Subsequently, dry in an oven to obtain the surface deactivated lithium titanate.

The deactivating groups with the structural formula of —O—P—$(OCH_2CH_3)(CH(CH_3)_2)_2$ are distributed on the surface of lithium titanate, and the deactivating groups are bonded with lithium titanate particles through the bond of Ti—O—P—$(OCH_2CH_3)(CH(CH_3)_2)_2$ and the bridge of $(Ti—O)_2P$—$(OCH_2CH_3)(CH(CH_3)_2)_2$.

Example 7

In a dry atmosphere, add 50 g of lithium titanate particles coated with $Al_2O_3$ on the surface and with a particle size of 100 nm into 250 mL of anhydrous N-methylpyrrolidone, and then stir at a rotation speed of 500 rpm for 30 min to obtain a homogeneously dispersed suspension. While stirring, add ethenyl dimethylphosphonate (where the mass ratio of ethenyl dimethylphosphonate to lithium titanate is 7.5:100), and when the addition is completed, keep the rotation speed constant to continue stirring for 1 h. When the reaction is completed, filter the reacted suspension through suction, place the solid obtained from the suction filtration into a beaker, add 100 mL of anhydrous N-methylpyrrolidone to wash, stir to disperse the solid, and then filter through suction. Repeat the filtering steps three times. Subsequently, dry in an oven to obtain the surface deactivated lithium titanate coated with $Al_2O_3$ on the surface and with the particle size of 100 nm.

The deactivating groups with the structural formula of —O—P—(CH=$CH_2$)($OCH_3$)$_2$ are distributed on the surface of lithium titanate, and the deactivating groups are bonded with lithium titanate particles through the bond of Ti—O—P—(CH=$CH_2$)($OCH_3$)$_2$ and the bridge of (Ti—O)$_2$P—(CH=$CH_2$)($OCH_3$)$_2$.

Example 8

In a dry atmosphere, add 50 g of lithium titanate particles coated with $Li_3PO_4$ on the surface and with a particle size of 150 nm into 250 mL of anhydrous methanol, and then stir at a rotation speed of 500 rpm for 30 min to obtain a homogeneously dispersed suspension. While stirring, add methyl ethyl n-propyl phosphate (where the mass ratio of methyl ethyl n-propyl phosphate to lithium titanate is 10:100), and when the addition is completed, keep the rotation speed constant to continue stirring for 1 h. When the reaction is completed, filter the reacted suspension through suction, place the solid obtained from the suction filtration into a beaker, add 100 mL of anhydrous methanol to wash, stir to disperse the solid, and then filter through suction. Repeat the filtering steps three times. Subsequently, dry in an oven to obtain the surface deactivated lithium titanate coated with $Li_3PO_4$ on the surface.

The deactivating groups with the structural formula of —O—P—($OCH_3$)($OCH_2CH_3$)($OCH_2CH_2CH_3$) are distributed on the surface of lithium titanate, and the deactivating groups are bonded with lithium titanate particles through the bond of Ti—O—P—($OCH_3$)($OCH_2CH_3$)($OCH_2CH_2CH_3$) and the bridge of (Ti—O)$_2$P—($OCH_3$)($OCH_2CH_3$)($OCH_2CH_2CH_3$).

Example 9

In a dry atmosphere, add 50 g of lithium titanate particles doped with Nb and with a particle size of 150 nm into 250 mL of anhydrous N-methylpyrrolidone, and then stir at a rotation speed of 500 rpm for 30 min to obtain a homogeneously dispersed suspension. While stirring, add diethenyl n-propylphosphinate (where the mass ratio of diethenyl n-propylphosphinate to lithium titanate is 5:100), and when the addition is completed, keep the rotation speed constant to continue stirring for 1 h. When the reaction is completed, filter the reacted suspension through suction, place the solid obtained from the suction filtration into a beaker, add 100 mL of anhydrous N-methylpyrrolidone to wash, stir to disperse the solid, and then filter through suction. Repeat the filtering steps three times. Subsequently, dry in an oven to obtain the surface deactivated lithium titanate doped with Nb.

The deactivating groups with the structural formula of —O—P—(O—$CH_2CH_2CH_3$)(CH=$CH_2$)$_2$ are distributed on the surface of lithium titanate, and the deactivating groups are bonded with lithium titanate particles through the bond of Ti—O—P—(O—$CH_2CH_2CH_3$)(CH=$CH_2$)$_2$ and the bridge of (Ti—O)$_2$P—(O—$CH_2CH_2CH_3$)(CH=$CH_2$)$_2$.

Example 10

In a dry atmosphere, add 50 g of lithium titanate particles doped with the element N and with a particle size of 150 nm into 250 mL of anhydrous N-methylpyrrolidone, and then stir at a rotation speed of 500 rpm for 30 min to obtain a homogeneously dispersed suspension. While stirring, add dimethyl ethyl phosphate (where the mass ratio of dimethyl ethyl phosphate to lithium titanate is 5:100), and when the addition is completed, keep the rotation speed constant to continue stirring for 2 h. When the reaction is completed, filter the reacted suspension through suction, place the solid obtained from the suction filtration into a beaker, add 100 mL of anhydrous N-methylpyrrolidone to wash, stir to disperse the solid, and then filter through suction. Repeat the filtering steps three times. Subsequently, dry in an oven to obtain the surface deactivated lithium titanate doped with N.

The deactivating groups with the structural formula of —O—P—($OCH_3$)$_2$($OCH_2CH_3$) are distributed on the surface of lithium titanate, and the deactivating groups are bonded with lithium titanate particles through the bond of Ti—O—P—($OCH_3$)$_2$($OCH_2CH_3$) and the bridge of (Ti—O)$_2$P—($OCH_3$)$_2$($OCH_2CH_3$).

Comparison Example 1

In a dry atmosphere, add 50 g of lithium titanate particles with a particle size of 10 nm into 250 mL of anhydrous ethanol, and then stir at a rotation speed of 500 rpm for 30 min to obtain a homogeneously dispersed suspension. Subsequently, keep the rotation speed constant to continue stirring for 3 h. When the reaction is completed, filter the reacted suspension through suction, place the solid obtained from the suction filtration into a beaker, add 100 mL of anhydrous ethanol to wash, stir to disperse the solid, and then filter through suction. Repeat the filtering steps three times. Subsequently, dry in an oven to obtain the lithium titanate with the particle size of 10 nm.

Comparison Example 2

In a dry atmosphere, add 50 g of lithium titanate particles coated with $Al_2O_3$ on the surface and with a particle size of 100 nm into 250 mL of anhydrous N-methylpyrrolidone, and then stir at a rotation speed of 500 rpm for 30 min to obtain a homogeneously dispersed suspension. Subsequently, keep the rotation speed constant to continue stirring for 1 h. When the reaction is completed, filter the reacted suspension through suction, place the solid obtained from the suction filtration into a beaker, add 100 mL of anhydrous N-methylpyrrolidone to wash, stir to disperse the solid, and then filter through suction. Repeat the filtering steps three times. Subsequently, dry in an oven to obtain the lithium titanate coated with $Al_2O_3$ on the surface and with the particle size of 100 nm.

Performance testing results of lithium ion batteries made with the surface modified lithium titanate in Examples 1-10 and the non-deactivated lithium titanate in Comparison Examples 1-2 will be provided.

(1) Mix homogeneously the surface modified lithium titanate obtained in Example 1, electrically conductive carbon, and polyvinylidene fluoride (PVDF) at a mass ratio of 90:5:5 with N-Methyl-2-pyrrolidone (NMP). Then coat the mixture as a film on aluminum foil to make patches as anodes. Subsequently use a lithium sheet as a cathode and polyethylene film as the isolation film, inject an ethylene carbonate (EC) and diethyl carbonate (DMC) (with the weight ratio at 1:1) electrolyte solution with 1 mol/L LiPF$_6$, and assemble into a button battery in a glove box with both oxygen and water contents below 0.1 ppm. Leave undisturbed for 12 h. Then install the button battery onto a Land battery tester for charging and discharging at a rate of 0.1 C and with a voltage range of 1.0 V-2.5 V. Stop after 5 cycles. Obtain the charging and discharging curves as shown in FIG. 1. It can be seen from FIG. 1 that the button battery made with the surface modified lithium titanate has flat charging and discharging plateaus and relatively high reversible capacity.

(2) Use the surface modified lithium titanate obtained in Examples 1-10 as the active substance. Mix homogeneously with NMP together with electrically conductive carbon and PVDF at a mass ratio of 90:5:5. Then coat the mixture as a film on aluminum foil to make patches as anodes. Use LiCoO$_2$ as cathodic active substance, mix homogeneously with NMP together with electrically conductive carbon and PVDF at a mass ratio of 90:5:3, then coat the mixture as a film on aluminum foil to make patches as cathodes. Use polyethylene film as the isolation film. Obtain cores for solution injection through cold pressing, piece cutting, winding, packaging, and hot air drying. Inject an EC and DMC (with the weight ratio at 1:1) electrolyte solution with 1 mol/L LiPF$_6$. The core model is 383450 (thickness 3.8 mm, width 34 mm, and length 50 mm). Charge the core to 2.8 V at 0.2 C, and then under the constant voltage of 2.8 V, charge to the current≤0.05 C to obtain lithium ion batteries assembled with the surface modified lithium titanate in Examples 1-10, which are numbered as S1-S10, respectively. Comparison Example 1 is a lithium ion battery that uses lithium titanate with no deactivating groups on the surface as the negative pole active substance (the positive pole active substance is LiCoO$_2$ as well) (numbered as D1), and Comparison Example 2 is a lithium ion battery that uses lithium titanate coated with aluminum oxide on the surface as the negative pole active substance (the positive pole active substance is LiCoO$_2$ as well) (numbered as D2).

Perform high temperature cycle performance tests on batteries numbered S1-S10, as well as D1 and D2: first, record the battery thickness d1 prior to the cycle, and then perform the cycle test at 60° C. in a voltage range of 1.5-2.8 V at the charging rate of 1 C and discharging rate of 1 C. After 500 cycles, record the battery thickness d2 again, and calculate its thickness expansion rate (d2−d1)/d1. The results are listed in Table 1.

Perform high temperature storage performance tests on batteries numbered S1-S10, as well as D1 and D2: first, record the battery thickness d3 prior to the storage, and then store at 85° C. for 4 h, record the battery thickness d4 after the storage, and calculate its thickness expansion rate (d4−d3)/d3. The results are listed in Table 1.

TABLE 1

Performance Testing Results for Examples 1-10 and Comparison Examples 1-2

| | Group | Type of organic phosphorus compounds | Thickness expansion rate after 500 cycles at 60° C. | Thickness expansion rate after 4 h of storage at 85° C. |
|---|---|---|---|---|
| Example 1 | S1 | trimethyl phosphate | 15% | 14% |
| Example 2 | S2 | n-octyl methyl ethylphosphonate | 12% | 11% |
| Example 3 | S3 | diethyl methylphosphinate | 8% | 9% |
| Example 4 | S4 | trimethylphosphine oxide | 5% | 6% |
| Example 5 | S5 | methyl ethyl n-propylphosphine oxide | 3% | 4% |
| Example 6 | S6 | diisopropyl ethylphosphinate | 4% | 5% |
| Example 7 | S7 | ethenyl dimethylphosphonate | 3% | 5% |
| Example 8 | S8 | methyl ethyl n-propyl phosphate | 2% | 4% |
| Example 9 | S9 | diethenyl n-propylphosphinate | 6% | 8% |
| Example 10 | S10 | dimethyl ethyl phosphate | 5% | 9% |
| Comparison Example 1 | D1 | None | 47% | 40% |
| Comparison Example 2 | D2 | None | 25% | 22% |

It can be seen from Table 1 that after the surface modification treatment on lithium titanate particles, the high temperature storage performance and high temperature cycle performance of lithium ion batteries made with the surface modified lithium titanate have been greatly improved, and the thickness expansion rates have all been greatly reduced. This is because deactivating groups present on the surface of exemplary lithium titanate can lower catalytic activity of the lithium titanate particles, thereby avoiding the occurrence of some surface catalytic reactions and consequently greatly reducing the probability of gas production by lithium titanate, reducing the gassing in lithium titanate batteries, reducing the thickness of expansion of the core during high temperature storage and high temperature cycle, and therefore improving the high temperature storage and high temperature cycle performance of lithium titanate batteries.

What is claimed is:

1. A lithium ion battery cathode, the lithium ion battery cathode comprising a surface modified lithium titanate wherein the surface modified lithium titanate comprises deactivating groups distributed on a surface of lithium titanate, wherein the deactivating groups are —O—P—RR'R", —O—P—(OR)R'R", —O—P—(OR)(OR')R", or —O—P—(OR)(OR')(OR"); R, R', and R" are identical or different C1~C8 alkyl or alkenyl groups; and the deactivating groups are bonded to the lithium titanate via a bond or a bridge.

2. A surface modified lithium titanate, comprising:
lithium titanate; and
deactivating groups distributed on a surface of the lithium titanate, wherein the deactivating groups are —O—P—RR'R", —O—P—(OR)R'R", —O—P—(OR)(OR')R", or —O—P—(OR)(OR')(OR"); R, R', and R" are identical or different C1~C8 alkyl or alkenyl groups, wherein the deactivating groups are bonded to the lithium titanate via a bond or a bridge, and wherein the lithium titanate is one or more of pure lithium titanate, lithium titanate having a surface coating and doped lithium titanate.

3. The surface modified lithium titanate as claimed in claim 2, wherein the surface coating comprises one or more of a metal oxide or composite oxide, aluminum phosphate, magnesium phosphate, lithium fluoride, lithium phosphate, or $LiMPO_4$, wherein the metal in the metal oxide or composite oxide is magnesium (Mg), aluminum (Al), silicon (Si), titanium (Ti), vanadium (V), zirconium (Zr), scandium (Sc), manganese (Mn), chromium (Cr), cobalt (Co), nickel (Ni), zinc (Zn), or cerium (Ce); and M in $LiMPO_4$ is Mg, iron (Fe), Co, Ni, Cr, Ti, or V.

4. The surface modified lithium titanate as claimed in claim 2, wherein the doped lithium titanate is lithium titanate doped with one or more of niobium (Nb), magnesium (Mg), zinc (Zn), lanthanum (La), zirconium (Zr), nitrogen (N), aluminum (Al), or yttrium (Y) ions.

5. The surface modified lithium titanate as claimed in claim 2, wherein a particle size of said lithium titanate having a surface coating is between 10 nm and 100 μm.

6. The surface modified lithium titanate as claimed in claim 5, wherein the particular size of said lithium titanate having a surface coating is between 50 nm and 1000 nm.

* * * * *